(12) United States Patent
Schürenberg et al.

(10) Patent No.: US 6,287,872 B1
(45) Date of Patent: Sep. 11, 2001

(54) SAMPLE SUPPORT PLATES FOR MALDI MASS SPECTROMETRY INCLUDING METHODS FOR MANUFACTURE OF PLATES AND APPLICATION OF SAMPLE

(75) Inventors: Martin Schürenberg, Tarmstedt; Jochen Franzen, Bremen, both of (DE)

(73) Assignee: Bruker Daltonik GmbH (DE)

( * ) Notice: Subject to any disclaimer, the term of this patent is extended or adjusted under 35 U.S.C. 154(b) by 0 days.

(21) Appl. No.: 09/208,081

(22) Filed: Dec. 9, 1998

(30) Foreign Application Priority Data

Dec. 11, 1997 (DE) .............................................. 197 54 978

(51) Int. Cl.$^7$ ....................................................... G01N 1/22
(52) U.S. Cl. ......................... 436/181; 422/100; 422/102; 422/104; 436/43; 436/173; 436/174; 436/180
(58) Field of Search .................................... 422/100, 102, 422/104; 436/43, 173, 174, 180, 181, 183

(56) References Cited

U.S. PATENT DOCUMENTS

| | | | |
|---|---|---|---|
| 5,041,266 | * | 8/1991 | Fox ........................................ 422/102 |
| 5,320,808 | * | 6/1994 | Holen et al. ............................ 422/64 |
| 5,498,545 | * | 3/1996 | Vestal ..................................... 436/47 |
| 5,770,860 | | 6/1998 | Franzen . |
| 5,828,063 | | 10/1998 | Köster et al. . |
| 5,831,184 | | 11/1998 | Willard et al. . |
| 5,958,345 | * | 9/1999 | Turner et al. ......................... 422/104 |

FOREIGN PATENT DOCUMENTS

| | | |
|---|---|---|
| 19618032 A1 | 11/1997 | (DE) . |
| 4-148699 | * 5/1982 | (JP) . |

OTHER PUBLICATIONS

O. Loo et al, Int. J. Mass Spectrom. Ion Processes 1997, 169/170, 273–290.*

Ole Vorm et al.; Improved Mass Accuracy in Matrix–Assisted Laser Desorption/Ionization Time–of–Flight Mass Spectrometry of Peptides; J Am Soc Mass Spectrom 1994, 5, pp. 955–958.

Daniel P. Little et al.; Maldi on a Chip: Analysis of Arrays of sub–to low–nL DNA Samples; DNA Diagnostics on a Chip: Apo B polymorphisms; pp. 11.

* cited by examiner

*Primary Examiner*—Arlen Soderquist

(57) ABSTRACT

The invention refers to sample support plates for the mass spectrometric analysis of large molecules, preferrable biomolecules, methods for the manufacture of such sample support plates and methods for loading the sample support plates with samples of biomolecules from solutions together with matrix substance for the ionization of the biomolecules using matrix-assisted laser desorption (MALDI).

The invention consists of making the surface of the sample support plate extremely hydrophobic, whereby a favorable structure of MALDI matrix crystals for effective ionization is generated when drying the sample droplets to sample spots. Using tiny, hydrophilic anchor areas for the sample droplets in this hydrophobic environment, the pipetting process is made much easier and the sample spots can be precisely located on the sample support plates. As the sample droplets are pipetted on, they are drawn to the hydrophilic anchors even if they are applied slightly imprecisely and they form, after drying, a precisely located, monolithic crystal conglomerate, which possesses favorable characteristics for the MALDI process. The method may particularly be used for oligonucleotide analysis using 3-hydroxypicolinic acid (3-HPA) as a matrix, but also for other MALDI preparation solutions of biomolecules.

13 Claims, 1 Drawing Sheet

SAMPLE SUPPORT PLATES FOR MALDI MASS SPECTROMETRY INCLUDING METHODS FOR MANUFACTURE OF PLATES AND APPLICATION OF SAMPLE

The invention refers to sample support plates for the mass spectrometric analysis of large molecules, preferrable biomolecules, methods for the manufacture of such sample support plates and methods for loading the sample support plates with samples of biomolecules from solutions together with matrix substance for the ionization of the biomolecules using matrix-assisted laser desorption (MALDI).

The invention consists of making the surface of the sample support plate extremely hydrophobic, whereby a favorable structure of MALDI matrix crystals for effective ionization is generated when drying the sample droplets to sample spots. Using tiny, hydrophilic anchor areas for the sample droplets in this hydrophobic environment, the pipetting process is made much easier and the sample spots can be precisely located on the sample support plates. As the sample droplets are pipetted on, they are drawn to the hydrophilic anchors even if they are applied slightly imprecisely and they form, after drying, a precisely located, monolithic crystal conglomerate, which possesses favorable characteristics for the MALDI process. The method may particularly be used for oligonucleotide analysis using 3-hydroxypicolinic acid (3-HPA) as a matrix, but also for other MALDI preparation solutions of biomolecules.

BACKGROUND OF THE INVENTION

For the analysis of large molecules, e.g. biomolecules, mass spectrometry with ionization by matrix-assisted laser desorption and ionization (MALDI) has become a standard method. For the most part, time-of-flight mass spectrometers (TOF-MS) are used for this purpose, but ion cyclotron resonance spectrometers (FT-ICR=Fourier transform ion cyclotron resonance) as well as high-frequency quadrupole ion trap mass spectrometers can be applied here. Normally, the biomolecules are in an aqueous solution. In the following, the high molecular weight substances including the biosubstances, the molecules of which are to be analyzed, are called "analytes".

The term biomolecules or biosubstances here mainly denotes the oligonucleotides (i.e. the genetic material in its various forms such as DNA or RNA) and the proteins (i.e. the essential building blocks of the living world), including their particular analogs and conjugates, such as glycoproteins or lipoproteins.

The choice of a matrix substance for MALDI is dependent upon the type of biomolecules; many more than a hundred different matrix substances have become known in the meantime. The task of the matrix substance is to separate the sample molecules from each other, to bond them to the sample support, to transform them into the gas phase during laser bombardment by the formation of a vapor cloud without destroying the biomolecules and if possible without attachment of the matrix molecules, and finally to ionize them there under protonation or deprotonation. It has proven favorable for this task to incorporate the analyte molecules in some form into the usually crystalline matrix substances during their crystallization or at least into the boundary-surfaces between the small crystals.

Various methods are known for applying the sample and matrix. The simplest of these is the pipetting of a solution with sample and matrix onto a clean, metal sample support plate. The solution drop is wetting on the metal surface an area, the size of which corresponds approximately to the diameter of the drop and is dependent on the hydrophilia of the metal surface and the characteristics of the droplet. After the solution dries, the sample spot consists of small matrix crystals spread over the formerly wet area, whereby generally there is no uniform coating of the wetted area. In aqueous solutions, most of the small crystals of the matrix generally begin to grow at the margin of the wet area on the metal plate. They grow toward the inside of the wet area. Frequently they form long crystals in radial direction, such as 5-dihydroxybenzoic acid (3-DHB) or 3-hydroxypicolinic acid (3-HPA), which peel off of the support plate toward the inside of the spot. The center of the spot is frequently empty or covered with fine small crystals which are however hardly utilizable for MALDI ionization due to the high concentration of alkali salts. The analyte molecules are irregularly distributed. This type of coating therefore demands visual observation of the sample support plate surface through a video microscope, which can be found on all commercially manufactured mass spectrometers for this type of analysis. Ion yield and mass resolution fluctuate in the sample spot from site to site. It is often a troublesome process to find a favorable location on the sample spot with good analyte ion yield and good mass resolution, and only experience and experimentation have been helpful here up to now.

For matrix substances which dissolve only very poorly or not at all in water, such as $\alpha$-cyano-4-hydroxycinnamic acid, it has proven favorable to create a very thin layer of crystals on the surface before applying the aqueous analyte solutions, for example by applying a solution of matrix substance in acetone. This type of MALDI coating is very successful for peptides (O. Vorm et al., J. Am. Soc. Mass Spectrum., 5, [1994], 955). In particular, the coating demonstrates site-independent sensitivity in the sample spot, a basic prerequisite for any automation of the analysis. Unfortunately, this type of homogenous preparation cannot be used for water soluble matrices, such as for oligonucleotides, for which 3-hydroxipicolinic acid (3-HPA) in an aqueous solution has proven to be the most favorable matrix up to now. However, this matrix demonstrates the edge effects described above in an extreme manner.

A favorable method for oligonucleotide sample loading is performed on silicon chips. The oligonucleotides bonded to the surface of the chips are bombarded with microdroplets of matrix solution (3-HPA) of only a few hundred picoliters using a piezo-operated micropipette, whereby a crystal structure with uniform MALDI sensitivity is generated (D. Little et al., paper presented at the 45th ASMS Conference on Mass Spectrometry and Allied Topics, Palm Springs, Jun. 2–5, 1997).

As described in patent DE 196 28 178, many sample spots can be applied in pipette robots onto a sample support with a high density using multiple pipettes through repeated transfer of samples from microtiter plates. However, the location accuracy of the sample spots is dependent on the precision of the sample robot. Commercially available sample robots, however, only have a mechanical precision of 200 micrometers at best. This application, without special preparation technique, leads to the above described irregular sample spots.

Even the methods for the MALDI technique indicated in the patent applications DE 196 17 011 and DE 196 18 032, using nitrocellulose, have not proven successful up to now for water soluble matrices and in particular for oligonucleotides.

But even when applying very small sample spots of reproducible sensitivity, it is a troublesome method to precisely determine the coordinates for the sample spots in the mass spectrometer, using only mass spectrometric means without any other auxiliary devices, if they have been applied inaccurately. Especially for a high sample throughput, it is therefore extremely desirable to know the location of the sample spots as exactly as possible before analysis. Only then fast automation becomes possible, meaning analysis of many samples without continuously performing control measurements. Especially advantageous would be application of the sample spots in a precise grid.

For a high sample throughput, automation of all analysis steps, including the preparation of the samples, is necessary. While sample preparation in pipette machines can proceed today very well automatically, the heterogeneity of MALDI preparations with water soluble matrices and the imprecise application of sample spots still strongly preclude automation of mass spectrometric measurement.

It is the objective of the invention to find a type of sample support enabling sample preparations which allow for automation of the mass spectrometric MALDI analyses of large molecules, especially biomolecules, forming precisely located sample spots with reproducible ionization yield. The sample spots should be arranged in a precisely located array, even if droplets are applied with a pipette robot that operates less precisely. Methods for favorable manufacture of such sample support plates and for loading the plates with samples must be found.

SUMMARY OF THE INVENTION

It is the basic idea of the invention to make the sample support surface extremely hydrophobic for the sample solution, i.e. for aqueous solutions. If a sample droplet containing dissolved analyte and matrix is applied to this surface, a completely different crystallization behavior results in the droplet than is known from previous preparations. The drop, situated on the hydrophobic surface without recognizable wetting of the surface, concentrates extremely when drying, and any possible small crystals forming in the inside are pressed together here by the force of the surface tension to a minimum volume. At the last moment of drying, as can be observed under a microscope, crystallization occurs all of a sudden, apparently by filling the gaps between already formed crystals; a monolithic lump with a microcrystalline grain structure thereby appears in the center of the area which the droplet had occupied.

This monolithic lump surprisingly demonstrates very good ionization of biomolecules, reproducible from lump to lump. The sensitivity is at least equal to that of the most favorable locations in previous preparations. The biomolecules are probably imbedded in a position at the grain boundaries of the microcrystalline grain structure, very favorable for the desorption and ionization process.

From a droplet of 500 nanoliters volume, having a diameter of one millimeter, a small flat block of about 200 micrometers diameter is created. This diameter corresponds somewhat to the standardly used cross section of the laser light beam focus. The monolithic lump is stuck to the hydrophobic base, however this bond is not very strong. The sample quantity used can be extremely reduced without a decrease in signal. Good signals can be obtained with sample spots cotaining far less than one femtomol of biomaterial. Classic preparation on hydrophilic surfaces would result in a spot diameter of at least one millimeter.

However, it is difficult to transfer the droplets onto the hydrophobic surface using a pipette. The droplet has the tendency to stick to the tip of the pipette, although the pipette normally is also made from a hydrophobic material. Precise depositing of the droplet onto the surface rarely succeeds.

Is therefore a further basic idea of the invention to provide the surface of the sample support with extremely small, hydrophilic anchor areas to attract the sample droplets and keep them, during drying, in the required array pattern for the sample spots. The diameter of these anchors should measure about a fifth of the diameter of the pipetted droplets, with a favorable range lying between half and a tenth of the diameter of the sample droplets being applied. The pipetted droplets with dissolved analyte molecules attach themselves to these tiny anchor areas. The pipette can be lifted away without taking the droplet with it. Even if the pipettes are applied with a slight lateral displacement, the droplet is situated as a sphere exactly over the hydrophilic anchor upon release from the pipette and dries there to form a monolithic microcrystal conglomerate. Only by slightly pressing the droplets is there an overlapping of the applied droplets onto the hydrophilic anchor areas. The hydrophilic anchors should have the exact form and size of the crystal conglomerate which is optimum for the MALDI process. A further advantage of these hydrophilic anchor areas is that the crystal conglomerates there bind quite solidly to the surface of the sample support.

Overall, automation of the analysis processes is achieved by the reproducible ion yield and high sensitivity, by the precision in sample location and by the solidly bound sample spots.

Figure 1:
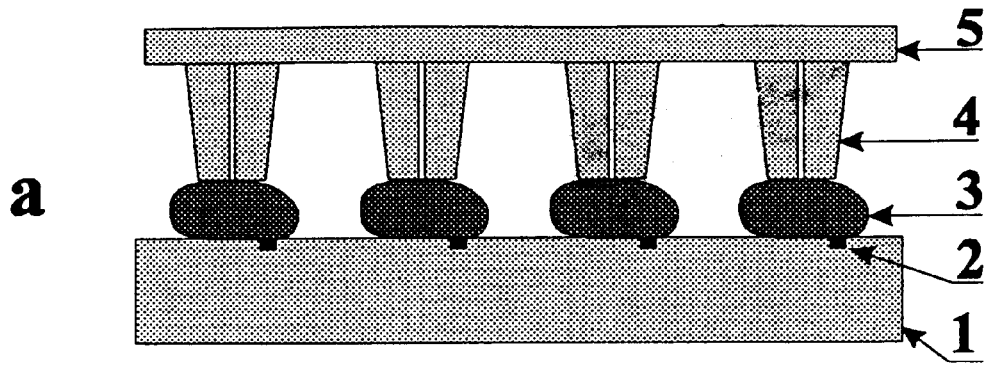
FIGS. 1a–1c show a sequence a, b, and c of schematic representations for applying the sample droplets (3) to the sample support (1) from the pipette tips (4) of a multiple pipette (5) with subsequent drying. The sequence steps are as follows.
Figure 1:
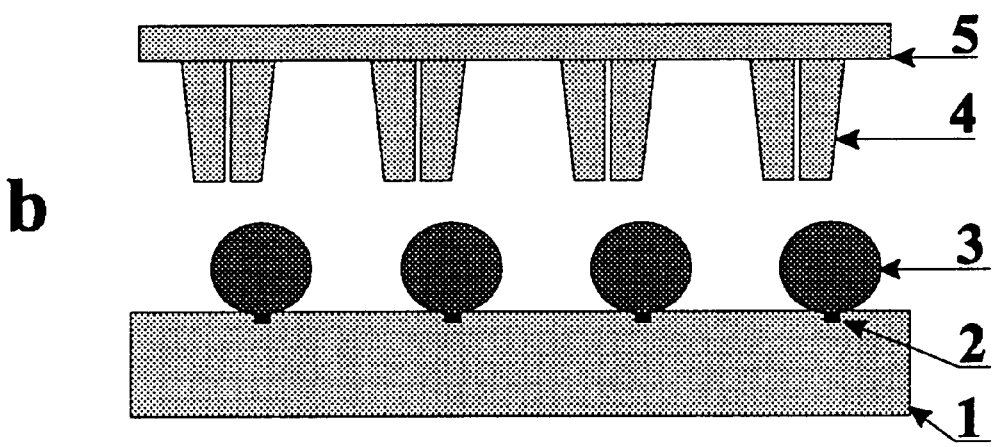
Figure 1:
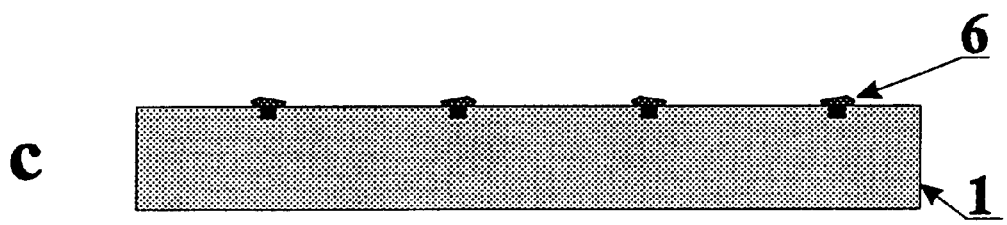

a. The pipettes have expressed the solution droplets (3) from their tips (4), the droplets (3) are pressed flat between pipette tips (4) and sample support (1). In this way the droplets reach their hydrophilic anchors (2), even if the pipette tips (4) are not precisely situated above the anchor area (2), and wet the sample support plate (1) there.

b. If the pipette tips (4) are raised, the droplets (3) take the form of spheres and are situated precisely above their hydrophilic anchors (2).

c. The sample droplets have dried and leave small monolithic blocks (6) of precise locational alignment with microcrystalline grain structure on the sample support (1).

DETAILED DESCRIPTION OF THE PREFERRED EMBODIMENTS

A "hydrophobic" surface in the sense of this invention is an unwettable and liquid-repellant surface for the sample liquid used, even if the liquid is not an aqueous solution. In the case of an oily sample solution, it should therefore correspondingly be a lipophobic surface. Normally, however, the biomolecules dissolve best in water, sometimes with the addition of organic, water-soluble solvents.

Correspondingly, a "hydrophilic" surface is understood to mean an easily wettable surface for the type of sample liquid used, even if the sample is not an aqueous solution.

In principle, the degree of hydrophobia can be determined from the setting angle which the liquid forms under standard conditions at the margin of the wetting area with the solid surface. However, it is possible for droplets on an extremely hydrophobic surface not to form any wetting area at all and thus also have no setting angle, such as is seen with mercury droplets on a glass or wood plate.

The surfaces of previously used metal sample support plates are normally slightly hydrophilic for aqueous sample solutions, and a sample droplet usually flows somewhat apart. The degree of hydrophilia is produced by the hydroxy groups which are created under the influence of moist air on any metal (even on precious metals).

To maintain hydrophobic surfaces on the sample support, the entire sample support can be produced from a hydrophobic material, for example Teflon©, which is both hydrophobic and lipophobic. However, it is necessary that the surface defines a constant electrical potential (for example by imbedding with graphite), since the MALDI process requires on the one hand a homogenous electrical field for uniform acceleration of the formed ion and, on the other hand, a dissipation of charges, the polarity of which opposes that of the ions formed. A pure graphite surface is also extremely hydrophobic.

It is certainly practical, for reasons of simple manufacture, to use sample support plates of metal or metallized plastic, and to make the surface hydrophobic. This can be done, for example, using a hydrophobic lacquer, or also by gluing on a thin, hydrophobic film, for example of Teflon©. However, it is even more practical to make the metal surface hydrophobic using a monomolecular chemical change, since a certain electrical conductivity, even if highly resistant, is then maintained.

Such hydrophobing of a metal surface is essentially known. For instance, longer alkane chains (for example, linear $C_{18}$ chains) are usually covalently bonded by a sulfur bridge to the atoms of the metal surface. This bond is extremely solid, and cannot be washed off using normal means. It resists years of exposure to weather. Surfaces that are even more hydrophobic are achieved if the hydrogen atoms are replaced by fluorine atoms at the end of the alkane chains. However, there are many equivalent methods of hydrophobing, for example using silicones, alkylchlorosilanes or tin-organic compounds.

An additional advantage of a surface prepared in this way also lies in the fact that metal and alkali ions can no longer be solved from the metal surface by the acidic matrix solutions and later deposited during the MALDI process as adducts to the biomolecule ions.

The production of a dense layer of such alkane chains on the metal surface is very simple in principle. To do this, the corresponding alkane thioles (alkane hydrogen sulfides) are first dissolved in methano. The metal plates are then immersed vertically in a water bath. If one drop of the methanolic solution of alkane thioles is added to the water, the alkane thioles move into an ordered formation on the surface of the water. All molecules are aligned in parallel in a very tight arrangement. The hydrophobic alkane ends are on the surface of the water bath, the hydrophilic thiole groups point into the water. If the metal plate is now pulled carefully out of the water, the closed formation of alkane thioles moves to the surface of the metal plate and creates covalent bonds of individual molecules with metal atoms of the surface while forming metal thiolates, at the same time maintaining the parallel orientation. The coating is dense.

The hydrophilic anchors for the sample droplets can be created in many ways. One example is to cover the required anchor areas with a washable or hydrophilic lacquer before hydrophobing the residual area. To create sufficiently small points, the covering lacquer can be shot in the form of tiny droplets using a piezo-operated droplet pipette in the manner of an ink-jet printer. Thus an extremely good location precision for the lacquer points is achieved. After hydrophobing, the lacquer points can be simply washed away, insofar as they do not already form sufficient good hydrophilic anchors as such. The washed anchors can also be made especially hydrophilic using special hydrophilization agents.

Such hydrophilic lacquer droplets can however also be imprinted subsequently onto the hydrophobic surface. To do this, especially amphiphilic substances are suitable which bond to the hydrophobic surface and create a hydrophilic surface.

The hydrophilic anchors can however also be created in a very simple manner by destruction of the hydrophobic layer. This can occur by imprinting (again in the manner of an ink-jet printer) chemically changing or enzymatically disintegrating substance solutions, by destruction using glowing hot burning tips, or also by ablation of surface material, for example using spark erosion or laser bombardment.

With longer storage, the hydrophilic anchor areas may easily become coated with hydrophobic molecules from the ambient air. It may therefore be practical to coat the hydrophilic anchors right after their production with a thin crystal layer of MALDI matrix substance. To do this, the surface of the metallic sample support may be briefly immersed in a dilute solution of matrix substance. Once lifted out, a precisely dosed droplet remains behind in every hydrophilic anchorage area. Drying of these droplets produces the desired crystal layers.

The sample droplets are normally applied to the sample support using pipettes, as shown schematically in FIG. 1. For simultaneous application of many sample droplets from microtiter plates, multiple pipettes are used, moved by pipette robots in pipette machines. It is therefore favorable to use sample support plates with the size of microtiter plates and to adapt the array of hydrophilic anchors to the well array of microtiter plates. It is also favorable if the sample support plates have the shape of microtiter plates, since they can then be processed by conventional pipette robots. Since a substantially higher density of samples can be achieved on the sample support than is possible in the microtiter plates, the array on the sample support plate can be much finer than that which corresponds to the array of wells on the microtiter plate. For example, this can be achieved by dividing the array distances of the microtiter plates by integer numbers. Then the samples from several microtiter plates can be applied to one sample support. The basic array of the original microtiter plate consists of 96 small wells, in distances of 9 millimeter from each other, arranged in 8 rows by 12 columns. The microtiter plates have been developed further without changing their dimensions. Modern embodiments have 384 or even 1,536 microwells in array patterns of 4.5 and 2.25 milimeters distances, respectively.

The horizontal location accuracy for positioning the multiple pipettes of the horizontally lying sample support is limited to about 200 micrometers. The vertical location accuracy can be improved slightly by lateral supporting surfaces on the multiple pipettes and stopping pins at about 50 micrometers.

The droplets are applied in an efficient manner if the multiple pipette is located at a distance of 500 micrometers above the sample support. About 500 nanoliters of sample solution are pipetted from every pipette tip of the multiple pipette onto the sample support as shown schematically in FIG. 1. Usually the amount of sample solution in the pipette tip is sealed off by a gas bubble, therefore there is no more solution present in the channel of the pipette tip afterward and the contact forces to the hydrophobic pipette tip are very minimal.

The droplets, which form spheres with a diameter of one millimeter in resting condition, are now pressed between the pipette tip and the sample support, as can be seen in FIG. 1a. Even with horizontal misadjustment of the pipette tips, the droplets can reach their respectively assigned hydrophilic anchor and attach themselves there. When the multiple pipette is lifted, the droplets remain on the sample support since they have found their attracting anchor there. They situate themselves precisely above the anchor and assume their ideal round form, as shown in FIG. 1b.

When drying, the droplets leave behind the crystal conglomerate with the samples molecules exactly on the hydrophilic anchors, as can be seen schematically in FIG. 1c. The lump-shaped MALDI preparations are therefore exactly positioned at known locations as required, and their size corresponds to the cross section of the laser beam focus. In addition, they offer a high yield of analyte ions and are thus ideally prepared for automatic analysis.

Of course, the droplets can be applied manually, as there are very many utilization possibilities for the sample support plates depicted here, as will be apparent to any specialist in this field according to these embodiments.

Consequential to the nature and objective of the drying process, specific compositions of sample solution must be avoided. Thus an addition of tensides or detergents is harmful, because wetting of the hydrophobic surface can take place in this way. Also addition of such organic solvents which cause wetting, must be avoided. Here too, any specialist will perceive according to these embodiments how he must conduct the method of sample preparation and pipetting in order to avoid faulty sample application.

Hydrophobic as well as hydrophilic surfaces can alter their wetting characteristics with lengthy storage in ambient air by coating of the surface with contaminants from the air. It is therefore practical to store the well prepared sample support plates in a vacuum or under protective gas.

What is claimed is:

1. A method of preparing samples for mass spectrometric analysis using matrix-assisted laser desorption (MALDI), the method comprising:

providing an electrically conductive sample support plate with a substantially flat surface and a plurality of anchor sites each of which is more hydrophilic than a hydrophobic area immediately surrounding it;

applying a liquid sample material to the sample support plate in droplets each of which is applied to the sample support plate in the vicinity of a different one of the anchor sites and is correspondingly drawn thereto, the droplets being at least twice as large in diameter as the anchor sites; and drying the sample liquid such that residual sample material from each droplet is concentrated onto the respective anchor site with which it is associated.

2. A method according to claim 1, wherein each anchor has a diameter which is between one half and one tenth of the diameter of the droplet with which it is associated.

3. A method according to claim 1, wherein the hydrophilic anchor areas form an array that corresponds to the basic well array of a microtiter plate with wells separated by distances of approximately nine millimeters.

4. A method according to claim 1, wherein the sample support plate has the size and form of a microtiter plate.

5. A method according to claim 1, wherein the plate comprises a hydrophobic base material.

6. A method according to claim 1 wherein providing a sample support plate comprises providing a sample support plate for which the loading surface of the plate has been made hydrophobic and the hydrophilic anchor areas overlay the hydrophobic surface.

7. A method according to claim 6, wherein hydrophobia on the sample support surface has been produced by a chemical change to the surface, by a lacquer-type film, by application of a polymer or by a glued-on film.

8. A method according to claim 6, wherein the hydrophilic anchor areas on the sample support have been produced by imprinting.

9. A method according to claim 6, wherein the hydrophilic anchor areas on the sample support have been produced by destroying the hydrophobia of the surface at the anchor sites.

10. A method according to claim 9, wherein the hydrophobia of the surface of the sample support has been destroyed at the anchor sites through chemical or enzymatic disintegration.

11. A method according to claim 1 wherein providing a sample support plate comprises providing a support plate that is manufactured from electrically conductive material, for which hydrophilic anchor areas are produced by imprinting a washable or already hydrophilic covering lacquer, and for which the remaining surface is made hydrophobic.

12. A method according to claim 1 wherein sample droplets are applied using hydrophobic pipette tips such that the sample droplets are pressed flat between the pipette tips and sample support and contact the appropriate hydrophilic anchor areas even with slight vertical misalignment of the pipette tips.

13. A method according to claim 12, wherein the sample droplets are applied simultaneously to the surface of the sample support with a multiple pipette.

\* \* \* \* \*